(12) United States Patent
Meindl et al.

(10) Patent No.: US 10,442,939 B2
(45) Date of Patent: Oct. 15, 2019

(54) METHOD FOR INCREASING THE SCRATCH RESISTANCE OF PLASTIC CUVETTES

(71) Applicant: Siemens Healthcare Diagnostics Products GmbH, Marburg (DE)

(72) Inventors: Josef Meindl, Bad Sodem am Taunus (DE); Oksana Pryshchepna, Hanau (DE)

(73) Assignee: Siemens Healthcare Diagnostics Products GmbH, Marburg (DE)

( * ) Notice: Subject to any disclaimer, the term of this patent is extended or adjusted under 35 U.S.C. 154(b) by 14 days.

(21) Appl. No.: 15/333,135

(22) Filed: Oct. 24, 2016

(65) Prior Publication Data

US 2017/0121539 A1 May 4, 2017

(30) Foreign Application Priority Data

Oct. 30, 2015 (EP) ................................ 15192277

(51) Int. Cl.
*C09D 7/63* (2018.01)
*B01L 3/00* (2006.01)
(Continued)

(52) U.S. Cl.
CPC ................ *C09D 7/63* (2018.01); *B01L 3/508* (2013.01); *B01L 3/5082* (2013.01);
(Continued)

(58) Field of Classification Search
CPC .. C09D 167/02; C09D 11/102; C09D 11/107; C09D 11/322; C09D 11/36; C09D 167/00; C09D 171/02; C09D 7/1233; C09D 7/63; C09D 5/14; C09D 5/1625; C09D 7/65; C09D 5/1637; C09D 189/00; C09D 5/008; C09D 5/1668; C09D 7/40; C09D 183/02; C09D 11/101; C09D 5/1618; C09D 7/61; C09D 11/32; C09D 7/67; C09D 5/00; C09D 5/16; C09D 5/1656; C09D 5/1681; C09D 5/1693; C09D 5/1675; C09D 7/1216; C09D 7/70; C09D 11/324; C09D 11/38; C09D 11/40; C09D 7/1266; C08L 67/02; C08L 2666/02; C08L 2666/14; C08L 2666/26; C08L 2201/06; C08L 3/02; C08L 67/025; C08L 67/04; C08L 71/02; C08L 89/00; C08L 27/12; C08L 2666/54; B01L 2200/12; B01L 2300/12; B01L 2300/16; B01L 13/508; B01L 3/5082; B01L 3/5027; B01L 3/508; G01N 2021/513; G01N 21/0303; G01N 21/51; G01N 35/10; G01N 2021/0389; G02B 1/14; G02B 5/23; A01N 25/10; A01N 37/46; A01N 63/02; C12Q 1/34; C12Q 1/44; C12Q 1/61; D06M 16/003; D06M 13/00; B29B 13/00; B29C 47/20; B29C 48/30; B29C 48/32; Y10T 428/24149; Y10T 442/2279; Y10T 428/25; Y10T 428/26; Y10T 428/24355; Y10T 428/24364; Y10T 428/265; Y10T 428/31504; Y10T 428/31663; A61L 15/24; A61L 27/34; A61L 33/064; A61L 15/34; A61L 15/42; A61L 15/46; A61L 2400/12; A61L 27/28; A61L 27/50; A61L 33/0094; B41J 2/2107; B01D 2325/06; B01D 69/02; B05D 3/002; B05D 5/00; B05D 5/083; B63B 59/04; B64D 15/00; B65D 25/14; C02F 1/44; C08G 18/10; C08G 18/3231; C08G 18/0823; C08G 18/6229; C08G 18/673; C08G 63/66; C08G 63/695; C08G 64/183; C08G 64/186; C08G 69/40; C10M 105/54; C10M 105/56; E04B 1/92; F01D 25/02; F01D 25/18; F15D 1/02; F15D 1/10; F16L 57/00; F28F 13/185; F28F 19/02; F28F 2245/04; H01L 31/02167; H01L 31/0236; Y02W 10/37; C08J 7/045; C08J 2475/00; C08J 7/047; C08J 7/123;
(Continued)

(56) References Cited

U.S. PATENT DOCUMENTS 5,989,692 A 11/1999 Brown
2012/0141785 A1* 6/2012 Lowrey .................... B05D 7/54
428/339

(Continued)

FOREIGN PATENT DOCUMENTS

| EP | 0787827 A2 | 8/1997 |
| EP | 2698626 A2 | 2/2014 |
| WO | WO 9803575 A1 | 1/1998 |

OTHER PUBLICATIONS

Münzing: "Additive für Oberfläche and Untergrund"; XP055266037; Found in the Internet: URL:http://www.munzing.com/uploads/media/EDAPLAN-LA-METOLAT-Additive-fuer-Oberflaeche-und-Untergrund.pdf; pp. 1-17; 2012.

(Continued)

*Primary Examiner* — Deborah K Ware
(74) *Attorney, Agent, or Firm* — Dugan & Dugan, PC

(57) ABSTRACT

In the field of consumable materials for automatic analytical instruments, a method for producing transparent plastic cuvettes with increased scratch resistance includes contacting exclusively an outer surface of the transparent plastic cuvette with a liquid comprising at least one surfactant or with a triglyceride and subsequently drying the outer surface such that scattered-light optical properties of the transparent plastic are not adversely affected.

10 Claims, 3 Drawing Sheets

(51) Int. Cl.
*C09D 171/02* (2006.01)
*G01N 21/03* (2006.01)
*G01N 21/51* (2006.01)
*G01N 35/10* (2006.01)
*G02B 1/14* (2015.01)

(52) U.S. Cl.
CPC ....... *C09D 171/02* (2013.01); *G01N 21/0303* (2013.01); *G01N 21/51* (2013.01); *G01N 35/10* (2013.01); *B01L 2200/12* (2013.01); *B01L 2300/12* (2013.01); *B01L 2300/16* (2013.01); *G01N 2021/0389* (2013.01); *G01N 2021/513* (2013.01); *G02B 1/14* (2015.01)

(58) Field of Classification Search
CPC ................ C08K 3/22; A61K 2800/412; A61K 2800/621; A61K 2800/622; A61K 2800/623; A61K 2800/624; A61K 8/0241; A61K 8/25; A61K 8/27; A61K 8/29; A61K 8/585; A61K 8/891; A61Q 19/08; B01J 13/14; C01P 2004/64; C01P 2006/12; C08F 220/18; C09B 67/0097; C09C 1/043; C09C 1/3684; C09C 3/00; C09C 3/063; C09C 3/08; C09C 6/10; C09K 15/08
See application file for complete search history.

(56) References Cited

U.S. PATENT DOCUMENTS

| | | | |
|---|---|---|---|
| 2014/0295563 A1 | 10/2014 | Matsuura | |
| 2015/0073069 A1* | 3/2015 | De Gans | C09D 183/08 523/435 |
| 2015/0191607 A1* | 7/2015 | McDaniel | C09D 5/008 424/409 |
| 2016/0002571 A1* | 1/2016 | Allen | A01N 25/30 504/358 |

OTHER PUBLICATIONS

European Search Report of European Application No. 15192277.0-1371 dated Apr. 29, 2016.

* cited by examiner

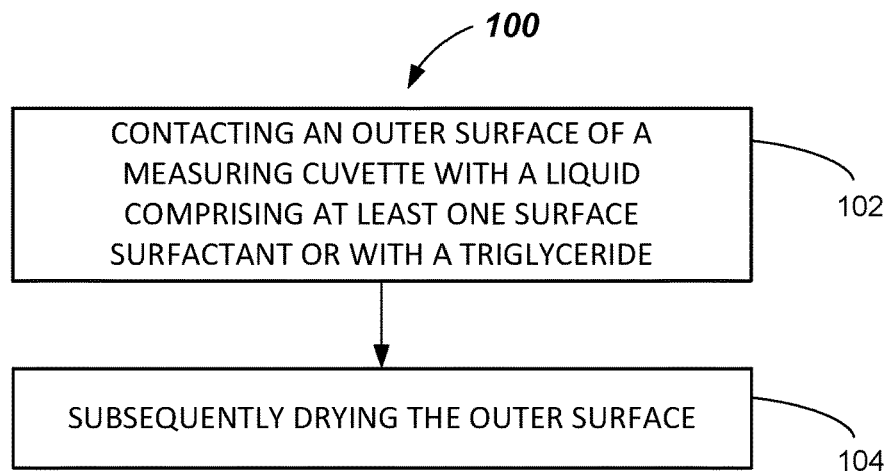
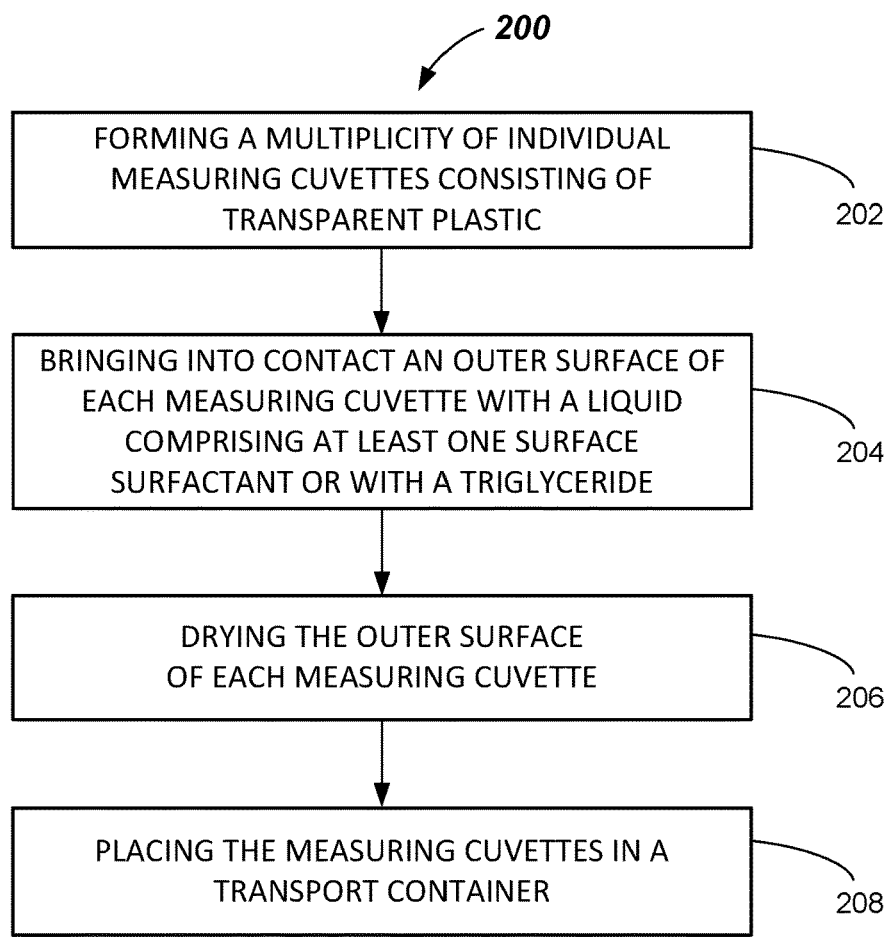

METHOD FOR INCREASING THE SCRATCH RESISTANCE OF PLASTIC CUVETTES

CROSS REFERENCE TO RELATED APPLICATION

This claims priority to European Patent Application No. EP 15192277.0, filed Oct. 30, 2015, which is hereby incorporated by reference herein in its entirety for all purposes.

FIELD

The present invention relates to the field of consumable materials for automatic analytical instruments and relates to a method for producing plastic cuvettes with increased scratch resistance.

BACKGROUND

Modern analytical instruments, such as are used routinely in analytics, forensics, microbiology and clinical diagnostics, are able to carry out multiple detection reactions and analyses with multiple samples. In order to be able to carry out automated multiple investigations, diverse automatically operating devices for the spatial transfer of measuring cuvettes, reaction containers and reagent liquid containers are required, such as transfer arms with grip function, conveyor belts or rotatable transport wheels, and also devices for the transfer of liquids such as pipetting devices. The instruments include a central control unit which, by means of appropriate software, is able to plan and execute the working steps for the desired analyses largely independently.

Many of the analytical methods used in such automated analytical instruments are based on optical methods. Particularly widespread are measuring systems which depend on photometric (e.g., turbidimetric, nephelometric, fluorometric or luminometric) or radiometric measuring principles. These methods enable the qualitative and quantitative detection of analytes in liquid samples without having to provide additional separation steps. The determination of clinically relevant parameters, such as the concentration or activity of an analyte, is carried out repeatedly by mixing an aliquot of a body fluid from a patient, simultaneously or sequentially, with one or more test reagents in a reaction vessel, whereby a biochemical reaction is initiated which effects a measurable change to an optical property of the test mixture.

The measurement result is in turn transmitted by the measuring system to a memory unit and evaluated. The analytical instrument subsequently delivers sample-specific data to a user via an output medium such as a monitor, a printer or a network connection.

The measuring cuvettes, in which the test mixtures are provided, transported and finally analyzed with the aid of an optical measurement method, are, in the simplest case, in the form of single units and typically consist of transparent plastic. The measuring cuvettes are generally disposable, that is they are provided as single-use articles, so that cleaning and the contamination risk linked thereto can be eliminated. However, the highest demands are placed on the quality of the measuring cuvettes, since even the smallest fluctuations, for example in the wall thickness, the diameter, the surface quality or the plastic composition, influence the optical properties of a measuring cuvette and therefore impair the precision of the optical analyses.

Modern analytical instruments can achieve a throughput of up to several hundred individual analyses per hour. Since one measuring cuvette is required for each individual analysis, the need for measuring cuvettes is correspondingly high. Therefore, in the analytical instruments, stock containers for measuring cuvettes are frequently provided which can take a relatively large number of measuring cuvettes in the form of a bulk good. The bulk good is typically delivered in plastic bags and is placed in the stock container of the analytical instrument by a user. Isolation mechanisms of various types ensure that one cuvette after another is removed from the stock container in order to then be available for a planned analysis. Such a stock container for cuvettes and a specific isolation mechanism are described, for example, in US-A1-2014/0295563.

It is problematic, however, that due to the storage and transport of the measuring cuvettes in the form of a bulk good, the cuvettes constantly rub against one another and thus the outer surface of individual cuvettes can be scratched. A scratched surface can however lead to undesired optical effects which, in particular in the case of scattered-light measurements, seriously impair the precision of an optical analysis.

This problem is solved in the prior art in different ways. One possibility is that the design of the cuvettes is adapted so that the region of the cuvette in which the optical measurement is carried out, i.e., the measuring window, is provided with a protecting raised frame so that at least the surface in the region of the measuring window is protected from scratching. Another possibility is that significantly more scratch resistant plastics such as cycloolefin copolymers are used instead of the polymethyl methacrylate and polystyrene plastics typically used.

The known solutions have the disadvantage, however, that they are relatively cost-intensive. Both the preparation of cuvettes with complicated architecture and the use of higher-value plastics increase the production costs in some cases by an order of magnitude.

SUMMARY

The object of the present invention, therefore, was to find the simplest and cost-effective means and methods with which the scratch resistance of conventional plastic cuvettes may be increased such that they can be stored and transported as a bulk good and without their suitability for use in optical analyses being impaired.

The object is achieved in accordance with the invention in that exclusively the outer surface of a measuring cuvette consisting of transparent plastic is brought into contact with a liquid comprising at least one surfactant and is subsequently dried. Alternatively, the outer surface of a measuring cuvette consisting of transparent plastic can be brought into contact with a triglyceride and can be subsequently dried.

The present invention therefore relates to a method for increasing the scratch resistance of a measuring cuvette consisting of transparent plastic, wherein exclusively the outer surface of the measuring cuvette is brought into contact with a liquid comprising at least one surfactant or with a triglyceride and is subsequently dried.

It has been found that conventional measuring cuvettes consisting, for example, of transparent polymethyl methacrylate or of polystyrene, after the treatment according to the invention, are more resistant to abrasion and therefore have an increased scratch resistance. The method according to the invention for increasing the scratch resistance is suitable, not exclusively but particularly, for measuring cuvettes consisting of transparent polystyrene or polymethyl methacrylate.

In the context of the present invention, the term "measuring cuvette" is understood to mean an essentially tubular container having a surrounding wall and an opening for receiving liquids to be analyzed. The cross section of the tube may have different shapes, for example round, polygonal, rectangular, quadratic, etc. Along the longitudinal axis of the tube, two or more sections may also be provided which have different cross-sectional shapes. Such measuring cuvettes are described, for example in EP-A2-2698626. The term "cuvette" implies that a measuring cuvette is provided for the optical analysis of a liquid to be analyzed. In the context of the present invention, a measuring cuvette has a layer thickness of at least 1 mm.

In the context of the present invention, the term "the outer surface of the measuring cuvette" is understood to mean the outer surface of the surrounding wall of the cuvette, whereas the inner surface of the measuring cuvette forms the cavity which is provided for receiving a liquid to be analyzed.

The bringing into contact of the outer surface of the measuring cuvette with a liquid comprising at least one surfactant or with a triglyceride can be carried out in various ways, e.g., by dipping, spraying, painting, rolling on.

Likewise, the outer surface of the measuring cuvette can subsequently be dried in different ways. Preference is given to air-drying owing to its simplicity.

The outer surface of the measuring cuvette is preferably brought into contact with a liquid comprising at least one non-ionic, one anionic, one cationic or one amphoteric surfactant.

A preferred non-ionic surfactant is a fatty alcohol alkoxylate, preferably a fatty alcohol alkoxylate from the group of polyoxyethylene(20) sorbitan monolaurate (trade name: Tween 20) and polyoxyethylene(20) sorbitan monooleate (trade name: Tween 80).

A preferred concentration of Tween 20 in the liquid which is brought into contact with the outer surface of the measuring cuvette is 0.5 to 2 percent by volume. To increase the scratch resistance of measuring cuvettes composed of polymethyl methacrylate, even a Tween 20 concentration of 0.5 percent by volume is suitable. To increase the scratch resistance of measuring cuvettes composed of polystyrene, a Tween 20 concentration of at least 1 percent by volume is suitable.

A preferred concentration of Tween 80 in the liquid which is brought into contact with the outer surface of the measuring cuvette is 0.5 to 2 percent by volume. To increase the scratch resistance of measuring cuvettes composed of polymethyl methacrylate, even a Tween 80 concentration of 0.5 percent by volume is suitable. To increase the scratch resistance of measuring cuvettes composed of polystyrene, a Tween 80 concentration of at least 1 percent by volume is suitable.

A further preferred non-ionic surfactant is an alkylphenol ethoxylate, preferably an alkylphenol ethoxylate from the group of 4-(1,1,3,3-tetramethylbutyl)phenyl-polyethylene glycol (trade name: Triton X-45), octoxynol 9 (trade name: Triton X-100) and nonylphenol polyethylene glycol ether (trade name: Tergitol NP-9).

A preferred concentration of Triton X-45 in the liquid which is brought into contact with the outer surface of the measuring cuvette is 0.5 to 3.5 percent by volume. To increase the scratch resistance of measuring cuvettes composed of polymethyl methacrylate, preferably a Triton X-45 concentration of 0.5 to 2 percent by volume is suitable. To increase the scratch resistance of measuring cuvettes composed of polystyrene, preferably a Triton X-45 concentration of 3 to 3.5 percent by volume is suitable.

A preferred concentration of Triton X-100 in the liquid which is brought into contact with the outer surface of the measuring cuvette is 0.5 to 2 percent by volume. To increase the scratch resistance of measuring cuvettes composed of polymethyl methacrylate, even a Triton X-100 concentration of 0.5 percent by volume is suitable. To increase the scratch resistance of measuring cuvettes composed of polystyrene, a Triton X-100 concentration of at least 1 percent by volume is suitable.

A preferred concentration of Tergitol NP-9 in the liquid which is brought into contact with the outer surface of the measuring cuvette is 0.5 to 2 percent by volume. To increase the scratch resistance of measuring cuvettes composed of polymethyl methacrylate, even a Tergitol NP-9 concentration of 0.5 percent by volume is suitable. To increase the scratch resistance of measuring cuvettes composed of polystyrene, a Tergitol NP-9 concentration of at least 1.5 percent by volume is suitable.

A further preferred non-ionic surfactant is an alkyl polyglycoside, preferably an alkyl polyglycoside from the group of benzyl-polyethylene glycol (1,1,3,3-tetramethylbutylphenyl) ether (trade name: Triton CF-10) and polyoxyethylene polyoxypropylene tert-C12-13-alkyl amine (trade name: Triton CF-32).

A preferred concentration of Triton CF-10 in the liquid which is brought into contact with the outer surface of the measuring cuvette is 0.5 to 2 percent by volume.

A preferred concentration of Triton CF-32 in the liquid which is brought into contact with the outer surface of the measuring cuvette is 0.5 to 2 percent by volume. To increase the scratch resistance of measuring cuvettes composed of polymethyl methacrylate, even a Triton CF-32 concentration of 0.5 percent by volume is suitable. To increase the scratch resistance of measuring cuvettes composed of polystyrene, a Triton CF-32 concentration of at least 1 percent by volume is suitable.

A preferred anionic surfactant is sodium dodecylsulfate or sodium stearate.

A preferred concentration of sodium dodecylsulfate in the liquid which is brought into contact with the outer surface of the measuring cuvette is 0.5 to 2 percent by weight. To increase the scratch resistance of measuring cuvettes composed of polymethyl methacrylate, even a sodium dodecylsulfate concentration of 0.5 percent by weight is suitable. To increase the scratch resistance of measuring cuvettes composed of polystyrene, a sodium dodecylsulfate concentration of at least 1 percent by weight is suitable.

A preferred concentration of sodium stearate in the liquid which is brought into contact with the outer surface of the measuring cuvette is 0.5 to 2 percent by weight. To increase the scratch resistance of measuring cuvettes composed of polymethyl methacrylate, even a sodium stearate concentration of 0.5 percent by weight is suitable. To increase the scratch resistance of measuring cuvettes composed of polystyrene, a sodium stearate concentration of at least 1 percent by weight is suitable.

A preferred cationic surfactant is distearyldimethylammonium chloride or an ester quat.

A preferred concentration of distearyldimethylammonium chloride in the liquid which is brought into contact with the outer surface of the measuring cuvette is 0.5 to 2 percent by weight. To increase the scratch resistance of measuring cuvettes composed of polymethyl methacrylate, even a distearyldimethylammonium chloride concentration of 0.5 percent by weight is suitable. To increase the scratch resistance of measuring cuvettes composed of polystyrene, a distearyldimethylammonium chloride concentration of at least 1 percent by weight is suitable.

A preferred amphoteric surfactant is lauryl sulfobetaine.

A preferred concentration of lauryl sulfobetaine in the liquid which is brought into contact with the outer surface of the measuring cuvette is 1 to 3.5 percent by weight. To increase the scratch resistance of measuring cuvettes composed of polymethyl methacrylate, preferably a lauryl sulfobetaine concentration of 1 to 2 percent by weight is suitable. To increase the scratch resistance of measuring cuvettes composed of polystyrene, preferably a lauryl sulfobetaine concentration of 3 to 3.5 percent by weight is suitable.

In a further embodiment of the method according to the invention, the outer surface of the measuring cuvette is brought into contact with a liquid comprising two or more of the aforementioned surfactants, preferably a combination of at least one surfactant from the group of the alkyl polyglycosides and at least one surfactant from the group of the fatty alcohol alkoxylates.

The liquid with which the outer surface of the measuring cuvette is brought into contact preferably consists of water and the at least one surfactant or the two or more surfactants, i.e., other than water and the surfactant(s), the liquid comprises no further notable constituents.

The water component of the liquid is preferably demineralized, deionized or distilled water. After drying, this causes no undesired residues to remain on the surface of the measuring cuvettes.

In a quite different variant of the method according to the invention, the outer surface of the measuring cuvette is brought into contact with a triglyceride.

Preferred triglycerides are vegetable fat or oil, particularly coconut fat.

The present invention furthermore provides a measuring cuvette composed of transparent plastic, preferably transparent polystyrene or polymethyl methacrylate, which is obtained by a method according to the invention. The outer surface of the measuring cuvettes according to the invention is coated with one or more surfactants or with a triglyceride. Measuring cuvettes according to the invention have increased scratch resistance compared to conventional measuring cuvettes.

The present invention furthermore provides a bulk good consisting of a multiplicity of measuring cuvettes according to the invention. The term "bulk good" in the context of the present invention is understood to mean that the individual measuring cuvettes can be moved freely relative to one another and are not secured in a certain position. A bulk good according to the invention preferably consists of 10 to 1000 measuring cuvettes.

The bulk good is preferably contained in a container, in a plastic bag, e.g., for transport or for storage or stockholding. The present invention therefore further provides a container comprising a bulk good according to the invention.

The present invention further relates to a method for providing a bulk good consisting of a multiplicity of measuring cuvettes consisting of transparent plastic. The method comprises the steps of:

a. forming a multiplicity of individual measuring cuvettes composed of the transparent plastic; then b. bringing into contact exclusively the outer surface of each measuring cuvette with a liquid comprising at least one surfactant or with a triglyceride; then c. drying the outer surface of each measuring cuvette;

d. placing the measuring cuvettes in a transport container.

The individual measuring cuvettes can be formed, for example, by a conventional injection molding process. The measuring cuvettes are preferably formed from polystyrene or polymethyl methacrylate.

The bringing into contact exclusively of the outer surface of each measuring cuvette with a liquid comprising at least one surfactant or with a triglyceride and the subsequent drying of the outer surface of each measuring cuvette does not necessarily have to, but should, be carried out as promptly as possible following the formation of the measuring cuvettes, so that the formation of scratches is prevented at the earliest possible stage. In any case, the surface treatment should be carried out, however, before placing the measuring cuvettes in a transport container in order to prevent increased abrasion arising between the movable cuvettes particularly during tipping of the measuring cuvettes into the transport container and also during transportation of the measuring cuvettes in the form of a bulk good.

The present invention further relates to the use of a measuring cuvette according to the invention in a method for the optical analysis of a liquid, wherein the liquid to be analyzed is present in a measuring cuvette according to the invention. The liquid can be human or animal body fluids such as blood, plasma, serum, sputum, exudate, bronchoalveolar lavage, lymphatic fluid, synovial fluid, seminal fluid, amniotic fluid, urine, spinal fluid, breast milk or extracts of hair, skin or tissue samples. Furthermore, the liquid can be cell culture samples, vegetable fluids, water and waste water samples, food or medicaments. If appropriate, the samples must be pretreated in order to make the analytes accessible to the detection method or to remove interfering sample constituents. Moreover, the liquid may of course take the form of a test mixture, that is a mixture of a sample with one or more test reagents. In such a test mixture a biochemical reaction takes place which causes a measurable change to an optical property of the test mixture which correlates with the analyte to be determined.

The present invention further relates to a method for the optical analysis of a liquid in an automatic analytical instrument, wherein the analytical instrument comprises a stock container comprising a multiplicity of measuring cuvettes according to the invention in the form of a bulk good. The method comprises for this purpose the following steps:

a. automatic withdrawal of an individual measuring cuvette from the stock container;

b. positioning the measuring cuvette in a receiving position;

c. filling the measuring cuvette with a liquid;

d. irradiating the liquid located in the measuring cuvette with light; and e. measuring the amount of light absorbed or scattered by the liquid.

The automatic withdrawal of an individual measuring cuvette from the stock container can be effected by means of any conventional isolation mechanism. The positioning of the measuring cuvette in a receiving position may be accomplished already by the isolation mechanism, or there is provided for example an automatic mobile transfer arm with a cuvette gripping device which grasps an individual cuvette, transports it to the desired target position and deposits it in a receiving position. The filling of the measuring cuvette with a liquid, for example with a liquid to be analyzed and with one or more test reagents, is preferably carried out using a pipetting device attached to an automatic movable or pivotable transfer arm. The liquid located in the measuring cuvette can be irradiated with light and the amount of light absorbed or scattered by the liquid can be measured in a variety of known ways.

The present invention further relates to an automatic analytical instrument comprising at least one optical measuring unit for the optical analysis of liquids located in measuring cuvettes, at least one stock container comprising a multiplicity of measuring cuvettes in the form of a bulk good, at least one device for the automatic withdrawal of an individual measuring cuvette from the stock container and for positioning the measuring cuvette in a receiving position, wherein a multiplicity of measuring cuvettes according to the invention are present in the stock container in the form of a bulk good.

BRIEF DESCRIPTION OF THE DRAWINGS

FIG. 1 illustrates a flowchart of a method for increasing the scratch resistance of a measuring cuvette according to embodiments of the invention.

FIG. 2 illustrates a flowchart of a method for providing a bulk good consisting of a multiplicity of measuring cuvettes according to embodiments of the invention.

DETAILED DESCRIPTION

Figure 3:
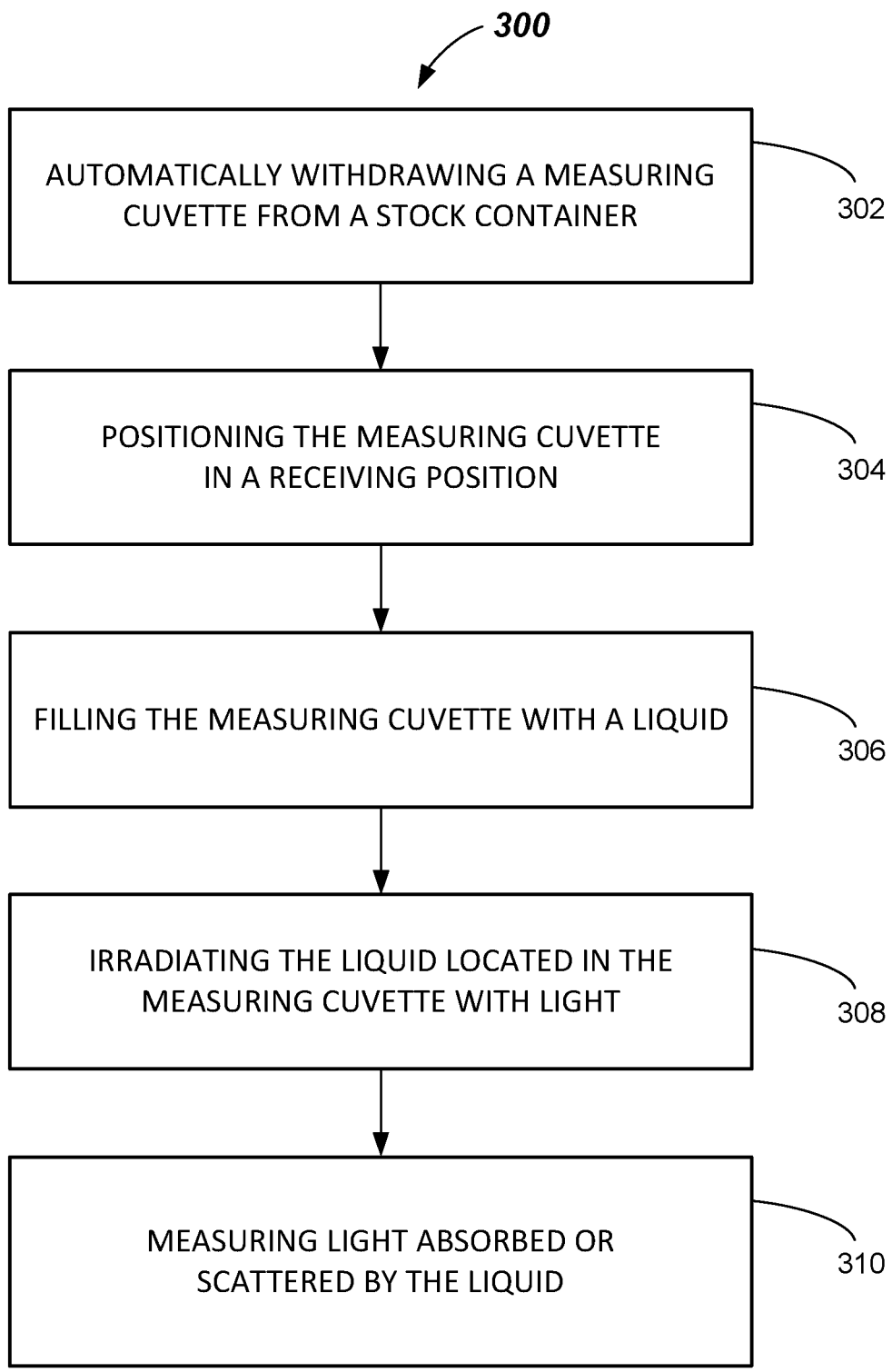
FIG. 3 illustrates a flowchart of a method for the optical analysis of a liquid in an automatic analytical instrument having a stock container comprising a multiplicity of measuring cuvettes in the form of a bulk good according to embodiments of the invention.
Figure 4:
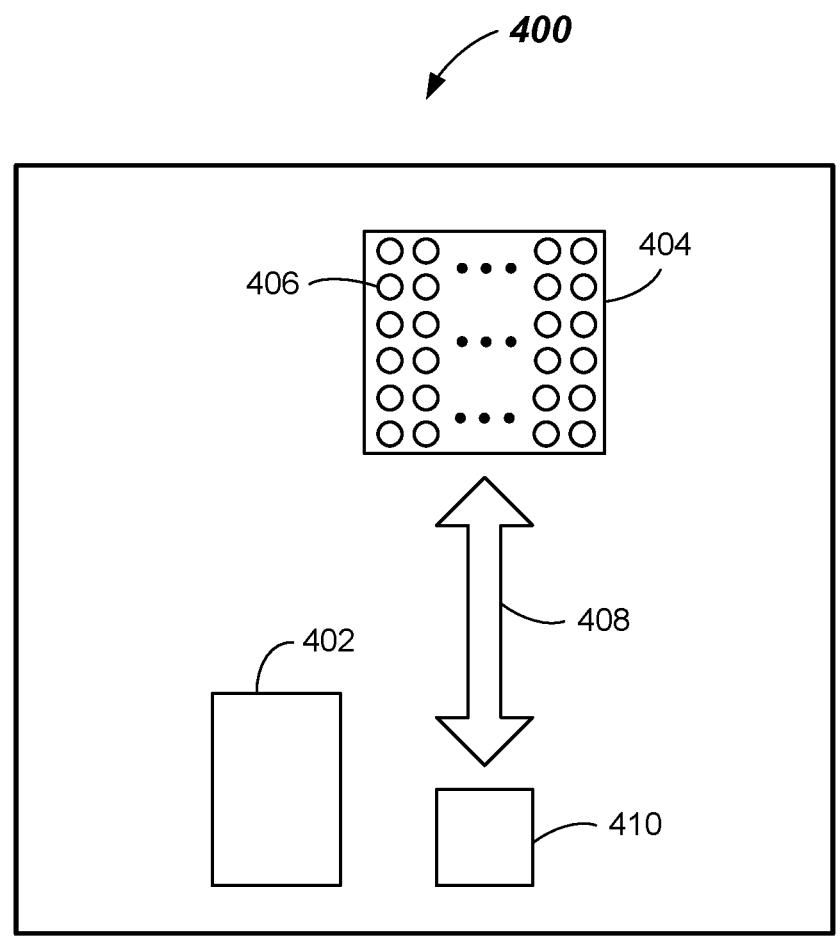
FIG. 4 illustrates an automatic analytical instrument according to embodiments of the invention.

The following working examples are intended to illustrate the invention by way of example and are not to be understood as limiting.

Example 1: Preparation of Measuring Cuvettes According to the Invention

To prepare the surfactant-containing liquids, the surfactants according to Table 1 were used.

TABLE 1

Surfactants used

| Surfactant | Trade or trivial name | Manufacturer |
|---|---|---|
| non-ionic: | | |
| Polyoxyethylene(20) sorbitan monolaurate | Tween 20 | BASF |
| Polyoxyethylene(20) sorbitan monooleate | Tween 80 | BASF |
| 4-(1,1,3,3-tetramethylbutyl) phenyl-polyethylene glycol | Triton X-45 | Sigma-Aldrich Chemie GmbH |
| Octoxynol 9 | Triton X-100 | Sigma-Aldrich Chemie GmbH |
| Nonylphenol polyethylene glycol ether | Tergitol NP-9 | Sigma-Aldrich Chemie GmbH |
| Benzyl-polyethylene glycol (1,1,3,3-tetramethylbutylphenyl) ether | Triton CF-10 | Stockmeier Chemie GmbH |
| Polyoxyethylene polyoxypropylene tert-C12-13-alkyl amine | Triton CF-32 | Stockmeier Chemie GmbH |
| amphoteric: | | |
| Lauryl sulfobetaine | — | Sigma-Aldrich Chemie GmbH |

TABLE 1-continued

Surfactants used

| Surfactant | Trade or trivial name | Manufacturer |
|---|---|---|
| anionic: | | |
| Sodium dodecylsulfate | — | BASF |
| Sodium stearate | — | Sigma-Aldrich Chemie GmbH |
| cationic: | | |
| Distearyldimethylammonium chloride | — | Sigma-Aldrich Chemie GmbH |

Defined amounts of the surfactants in solid form were weighed out and defined amounts of the surfactants in liquid form were taken up using a metering pipette and in each case dissolved in distilled water such that aqueous solutions were obtained with defined surfactant concentrations (percent by volume [% (v/v)] or percent by weight [% (w/w)]).

Commercially available tubular measuring cuvettes (circular cross section, internal diameter 7 mm, wall thickness 0.7 mm, height 30.5 mm) consisting of polystyrene or polymethyl methacrylate were each briefly dipped in a surfactant-containing liquid (for ca. 0.5-2 seconds) with the opening facing upwards such that the outer surface was wetted with liquid to just below the upper edge of the cuvette and no liquid was able to enter the interior of the measuring cuvette. After withdrawal from the liquid, the cuvettes were placed on an absorbent piece of blotting paper with the opening facing downwards and dried at room temperature for at least 20-40 minutes.

Example 2: Determination of the Scratch Resistance of Measuring Cuvettes According to the Invention The measuring cuvettes prepared according to Example 1 were investigated in abrasion experiments. For this purpose, two identically coated cuvettes, i.e., treated with the same surfactant-containing solution, were each fixed tension-free in two holders of a testing device and arranged one on top of the other so that the surfaces of the cuvettes came to lie plane-parallel in the abrasion test. The holder for the upper cuvette is designed to be stationary; the holder for the lower cuvette is arranged on a horizontally movable sample table. During the abrasion test, the upper cuvette was lowered onto the lower cuvette and a test force of 20 N was generated (from an estimate of the practical loading, appearance of scratches can be expected from a force of ca. 1 N). For the sample table on which the lower cuvette had been arranged, a travel path of ca. 10 mm was set and the upper cuvette was traversed by the lower cuvette in one direction twice with a test force of 20 N. The friction traces thereby generated on the surfaces of the upper and the lower cuvette were examined by light microscopy and the increased scratch resistance and resulting improved wear resistance compared to uncoated cuvettes was assessed by the investigator.

It was observed that layered smeared areas with extensive diffusion resulted on the surface of the upper stationary cuvette due to the friction contact, whereas in the lower moving cuvette on the other hand, line-shaped signs of wear formed in the direction of travel which ranged from fine lines up to extensive streak-like damage to the surface. Based on these features, the qualitative estimation of the improvement to the wear resistance (scratch resistance)

compared to uncoated cuvettes was undertaken. The following quality evaluations were used:

"+++" for "very good" improvement to the wear resistance;
"++" for "good" improvement to the wear resistance;
"+" for "moderate" improvement to the wear resistance;
"−" for "no" improvement to the wear resistance.

The results of the qualitative evaluation of the wear resistance of the variously coated polystyrene or polymethyl methacrylate cuvettes are shown in Tables 2 and 3.

TABLE 2

Qualitative evaluation of the wear resistance of coated polymethyl methacrylate cuvettes

| Surfactant concentration of the surfactant-containing solution | Wear resistance | |
| --- | --- | --- |
| | upper cuvette | lower cuvette |
| Tween 20, 0.5% (v/v) | ++ | ++ |
| Tween 20, 1% (v/v) | ++ | ++ |
| Tween 80, 0.5% (v/v) | ++ | +++ |
| Triton X-45, 0.5% (v/v) | ++ | ++ |
| Triton X-100, 0.5% (v/v) | ++ | +++ |
| Tergitol NP-9, 0.5% (v/v) | ++ | +++ |
| Triton CF-10, 0.5% (v/v) | ++ | +++ |
| Triton CF-32, 0.5% (v/v) | ++ | +++ |
| Lauryl sulfobetaine, 1% (w/w) | ++ | ++ |
| Distearyldimethylammonium chloride, 0.5% (w/w) | ++ | ++ |
| Sodium dodecylsulfate, 0.5% (w/w) | + | ++ |
| Sodium stearate, 0.5% (w/w) | + | + |

Table 2 indicates that with every surfactant-containing liquid tested an improvement in the scratch resistance of the surface of polymethyl methacrylate cuvettes is achieved.

TABLE 3

Qualitative evaluation of the wear resistance of coated polystyrene cuvettes

| Surfactant concentration of the surfactant-containing solution | Wear resistance | |
| --- | --- | --- |
| | upper cuvette | lower cuvette |
| Tween 20, 1% (v/v) | + | + |
| Tween 20, 2% (v/v) | + | + |
| Tween 80, 1% (v/v) | ++ | ++ |
| Triton X-45, 3.34% (v/v) | + | + |
| Triton X-100, 1% (v/v) | + | + |
| Tergitol NP-9, 1.43 % (v/v) | + | + |
| Triton CF-10, 0.5% (v/v) | + | ++ |
| Triton CF-32, 1% (v/v) | + | ++ |
| Lauryl sulfobetaine, 3.34% (w/w) | + | + |
| Distearyldimethylammonium chloride, 1% (w/w) | +− | ++ |
| Sodium dodecylsulfate, 1% (w/w) | +− | ++ |
| Sodium stearate, 1% (w/w) | + | + |

Table 3 indicates that with every surfactant-containing liquid tested an improvement in the scratch resistance of the surface of polystyrene cuvettes is achieved.

LIST OF REFERENCES 100, 200, 300 methods
102, 104 method steps
202, 204, 206, 208 method steps
302, 304, 306, 308, 310 method steps
400 automatic analytical instrument
402 optical measuring unit
404 stock container
406 measuring cuvette
408 device for automatic withdrawal of an individual measuring cuvette
410 receiving position

What is claimed is:

1. A method for increasing the scratch resistance of a measuring cuvette consisting of transparent plastic, the method comprising:
    contacting exclusively to an outer surface of the measuring cuvette a liquid consisting of water and at least one surfactant; and
    subsequently drying the outer surface.

2. The method as claimed in claim 1, wherein the surfactant is selected from at least one non-ionic, one anionic, one cationic, or one amphoteric surfactant.

3. The method as claimed in claim 2, wherein the non-ionic surfactant is a fatty alcohol alkoxylate selected from the group consisting of polyoxyethylene(20) sorbitan monolaurate (Tween 20) and polyoxyethylene(20) sorbitan monooleate (Tween 80).

4. The method as claimed in claim 2, wherein the non-ionic surfactant is an alkylphenol ethoxylate selected from the group consisting of 4-(1,1,3,3-tetramethylbutyl) phenyl-polyethylene glycol (Triton X-45), octoxynol 9 (Triton X-100), and nonylphenol polyethylene glycol ether (Tergitol NP-9).

5. The method as claimed in claim 2, wherein the non-ionic surfactant is an alkyl polyglycoside selected from the group consisting of benzyl-polyethylene glycol (1,1,3,3-tetramethylbutylphenyl) ether (Triton CF-10) and polyoxyethylene polyoxypropylene tert-C12-13-alkyl amine (Triton CF-32).

6. The method as claimed in claim 2, wherein the anionic surfactant is sodium dodecylsulfate or sodium stearate.

7. The method as claimed in claim 2, wherein the cationic surfactant is distearyldimethylammonium chloride or an ester quat.

8. The method as claimed in claim 2, wherein the amphoteric surfactant is lauryl sulfobetaine.

9. The method as claimed in claim 1, wherein the liquid comprises two or more surfactants including at least one alkyl polyglycoside and at least one fatty alcohol alkoxylate.

10. The method as claimed in claim 1, wherein the measuring cuvette consists of a plastic selected from the group consisting of polystyrene and polymethyl methacrylate.

* * * * *